United States Patent [19]
Chapman et al.

[11] Patent Number: 5,753,738
[45] Date of Patent: May 19, 1998

[54] ETHER COSOLVENTS FOR RESIN FORMULATIONS

[75] Inventors: Richard George Chapman, Weybridge; Nicholas John Hazel, Beverley; Nevin John Stewart, Guildford; Stephen Paul Goodwin, London; Andrew Richard Lucy, Hotham, all of England

[73] Assignee: BP Chemicals Limited, London, England

[21] Appl. No.: 495,518
[22] PCT Filed: Dec. 13, 1994
[86] PCT No.: PCT/GB94/02722
  § 371 Date: Dec. 22, 1995
  § 102(e) Date: Dec. 22, 1995
[87] PCT Pub. No.: WO95/17461
  PCT Pub. Date: Jun. 29, 1995

[30] Foreign Application Priority Data
Dec. 23, 1993 [GB] United Kingdom ............... 9326325

[51] Int. Cl.⁶ ..................................................... C08K 5/06
[52] U.S. Cl. ..................... 524/376; 524/367; 524/369
[58] Field of Search ............................. 524/367, 376, 524/369

[56] References Cited

U.S. PATENT DOCUMENTS

| | | | |
|---|---|---|---|
| 3,446,764 | 5/1969 | Phillips et al. | 524/376 X |
| 4,460,734 | 7/1984 | Owens et al. | 524/376 |
| 4,523,922 | 6/1985 | Ong et al. | 524/376 X |
| 5,374,305 | 12/1994 | Glancy et al. | 524/377 X |

*Primary Examiner*—Judy M. Reddick
*Attorney, Agent, or Firm*—Fay, Sharpe, Beall, Fagan, Minnich & McKee

[57] ABSTRACT

This invention relates to aqueous resin formulations comprising as cosolvent an alkoxy ethoxyethanol which (i) has 4–8 carbon atoms in the alkoxy group, (ii) has a boiling point at atmospheric pressure within the range from 200° to 350° C. and (iii) in mixtures with n-heptane in the ratio of 30:70 by weight respectively has specific miscibility characteristics. The cosolvent acts either as a solvent or coalescing aid in aqueous formulations used as coatings and paints.

3 Claims, No Drawings

ETHER COSOLVENTS FOR RESIN FORMULATIONS

This invention relates to the use of specific alkoxy ethoxyethanols as cosolvent in aqueous resin formulations.

It is well known that some resins used for water-based coatings are largely incompatible with water, and that the compatibility with water can be improved by the addition of an organic solvent known as a "coupling solvent". The nature of the coupling solvent used can affect the performance of the formulated coating in several ways.

The "coupling power" of the solvent relates to how good the solvent is at increasing the solubility of the resin in water. A solvent good in this respect can, among other benefits, increase the range of humidity and/or temperature at which the coating may be successfully applied. A simple measure of the "coupling power" of the solvent may be obtained by adding water to a 30:70 by weight mixture of coupling solvent and n-heptane at room temperature, where the heptane acts as a model for an oleophilic resin. At some point as water addition is increased, the mixture moves from a single, homogeneous phase to a mixture of two phases. The amount of water added before the appearance of the second phase is an indication of the coupling power of the solvent. The objective is to maximise the amount of water that can be added to the coupling solvent before the second phase appears.

The rheology of a coating formulation is partly determined by the composition and phase behaviour of the water/resin/coupling solvent ternary mixture. A good coupling solvent can influence the rheology such that, eg, the process of formulating the coating is simplified by minimising viscosity variations when a solution of the resin in the coupling solvent is diluted with water. Effectively, it is believed that the coupling solvent associates preferentially with the organic phase rather than the aqueous phase. A good solvent can also improve the performance of the coating when applied to a substrate by, eg, reducing sagging and curtaining effects. Desirable rheological behaviour is related to the composition of the ternary mixture such that, when two liquid phases coexist, one of the phases should be very largely comprised of water. This behaviour is easily determined using a model system with n-heptane and carrying out the test to measure coupling power as described above. When just sufficient water is added so that a second phase begins to appear as signified by the formation of small droplets, these droplets are largely comprised of water whereas the larger organic phase comprises mainly n-heptane and the coupling solvent (shown as notation (d) in the Table below); the behaviour would be considered undesirable if two phases are formed which are comparable in volume and one of the phases is largely comprised of n-heptane (shown as notation (nd) in the Table below).

A coupling solvent for use in coatings should have a higher boiling point than water such that the coupling solvent allows a film of the coating applied on a substrate to dry as a continuous phase, ie the water evaporates faster than the solvent.

Hitherto, among high-boiling (200°–350° C.) coupling solvents, 2-(2-butoxyethoxy)ethanol (hereafter "BDGE"), which boils at 231° C., has been the most commonly used monoalkyl diglycol ether coupling solvent, whilst hexyl glycol ether, which boils at 208° C. has also been used. It has now been found that specific ethers of diethylene glycol perform just as well if not better than these solvents when used as coupling solvents in aqueous resin formulations in respect of their phase behaviour and/or their coupling power.

Accordingly, the present invention is an aqueous resin formulation comprising as cosolvent an alkoxy ethoxyethanol characterised in that, the alkoxy ethoxyethanol:

i. has 4–8 carbon atoms in the alkoxy group, ii. has a boiling point at atmospheric pressure within the range from 200° to 350° C. and iii. in mixtures with n-heptane in the ratio of 30:70 by weight respectively, either
   a. does not cause phase separation, (ie the mixture remains homogeneous) until more than 2.5% wt/wt of water is added, and/or,
   b. phase separation occurs in the form of droplets upon addition of at least 1.5% wt/wt of water, said droplets having >50% wt/wt of water.

Specific examples of the compounds which represent the cosolvents of the present invention include:

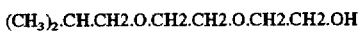

ie isobutoxy ethoxyethanol (hereafter "iBDGE").

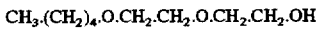

ie n-pentoxy ethoxyethanol (hereafter ("n-PDGE").

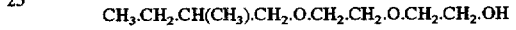

ie 2-methylbutoxy ethoxyethanol (hereafter "2-MBDGE"), $CH_3.CH.(CH_3).CH_2.CH_2.O.CH_2.CH_2.O.CH_2.CH_2.OH$ ie 3-methylbutoxy ethoxyethanol (hereafter "3-MBDGE"),

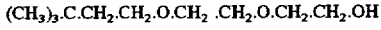

ie 3,3-dimethylbutoxy ethoxyethanol (hereafter "3,3-DMBDGE") and $Cyclohexyl.CH_2.O.CH_2.CH_2.O.CH_2.CH_2.OH$ ie cyclohexylmethyleneoxy ethoxyethanol (hereafter "CHMDGE").

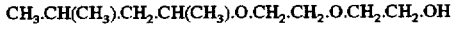

ie 4-Methylpent-2-oxy ethoxyethanol (hereafter "MIBCDGE")

$CH_3.(CH_2)_5.O.CH_2.CH_2.O.CH_2.CH_2.OH$ ie n-hexoxy ethoxyethanol (hereafter "n-HDGE") and

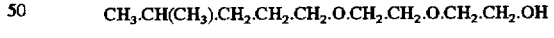

ie 4-methylpentoxy ethoxyethanol (hereafter "4-MPDGE")

These compounds exhibit the desired phase behaviour and/or desirable coupling power when used as cosolvents in aqueous resin formulations used for coatings or in paints.

Of these compounds, 2-methylbutoxy ethoxyethanol, 3,3-dimethylbutoxy ethoxyethanol and cyclohexylmethyleneoxy ethoxyethanol are new compounds which have not been reported in literature hitherto. Brief methods of preparations of these compounds and properties thereof are given below.

For instance, 2-MBDGE can be synthesised by the dropwise addition of 1-chloro-2-methylbutane to a stirred mixture of a molar excess of diethylene glycol and an equimolar amount of an aqueous alkali, eg sodium hydroxide, at elevated temperature under cover of a gas inert under the reaction conditions eg nitrogen. The reaction mixture is maintained at this elevated temperature over a period and then cooled. The cold reaction mixture is then extracted with a suitable solvent such as eg dichloromethane. The resultant extract in the solvent is washed repeatedly with eg water, dried and subjected to fractional distillation, suitably under a high vacuum when 2-MBDGE is collected as a colourless mobile liquid emerging at eg 82° C./1 mm Hg. 2-MBDGE has a boiling point of about 240° C. and was characterised by $^{13}$C NMR spectroscopy.

Similarly, 3,3-DMBDGE is an ether which can be synthesised by the dropwise addition of 1-chloro-3,3-dimethylbutane to a stirred mixture of a molar excess of diethylene glycol and an equimolar amount of an aqueous alkali, eg sodium hydroxide, at elevated temperature under cover of a gas inert under the reaction conditions eg nitrogen. The reaction mixture is maintained at this elevated temperature over a period and then cooled. The cold reaction mixture is then extracted with a suitable solvent such as eg dichloromethane. The resultant extract in the solvent is washed repeatedly with eg water, dried and subjected to fractional distillation, suitably under a high vacuum when 3,3-DMBDGE is collected as a colourless mobile liquid emerging at eg 118° C./9 mm Hg. 3,3-DMBDGE was characterised by $^{13}$C NMR spectroscopy.

Again, CHMDGE can be synthesised by the dropwise addition of cyclohexylmethyl bromide to a stirred mixture of a molar excess of diethylene glycol and an equimolar amount of an aqueous alkali, eg sodium hydroxide, at elevated temperature under cover of a gas inert under the reaction conditions eg nitrogen. The reaction mixture is maintained at this elevated temperature over a period and then cooled. The cold reaction mixture is then extracted with a suitable solvent such as eg dichloromethane. The resultant extract in the solvent is washed repeatedly with eg water, dried and subjected to fractional distillation, suitably under a high vacuum when CHMDGE is collected as a colourless mobile liquid emerging at eg 144° C./8 mm Hg. CHMDGE was characterised by $^{13}$C NMR spectroscopy.

Similarly, MIBCDGE can be synthesised by the dropwise addition of tetrahydro-2-[2-(2-chloroethoxy)-ethoxy]-2H-pyran to a pre-formed stirred solution of sodium 4-methylpent-2-oxide in a dry solvent such as 1,2-dimethoxyethane at elevated temperature under cover of a gas inert under the reaction conditions eg nitrogen. The reaction mixture is maintained at this or slightly higher elevated temperature over a period and then cooled. The cold reaction mixture is then filtered and to the crude reaction mixture an excess of an alcohol such as methanol is added together with an acidic ion exchange resin. When the temperature of this mixture is raised eg to about 40°–50° C. with stirring and maintained under these conditions for about an hour, transacetalisation occurs. Thereafter, the solvent is removed from the reaction mixture under basic conditions. This transacetalisation process is repeated twice more and MIBCDGE is isolated by fractional distillation, suitably under a high vacuum when MIBCDGE is collected as a colourless mobile liquid emerging at eg 80° C./0.4 mm Hg. MIBCDGE was characterised by $^{13}$C NMR spectroscopy.

As regards the other compounds in this list, most of these are commercially available material and can be purchased from Aldrich Chemical Co Ltd, or Fluka Chemicals Ltd or can be prepared by suitable choice of reactants in the general synthetic methods described below.

The surprising aspect of the invention may be seen in Table 1 below by comparing the performance in respect of coupling power and phase behaviour of MIBCDGE with that of other high-boiling coupling solvents, for example 2-(2-butoxyethoxy)ethanol (hereafter "BDGE") and hexyl glycol ether (hereafter "HGE"). It will be seen that the following solvents show desirable phase behaviour like HGE but better coupling power than either HGE or BDGE: 2-MBDGE and 3,3-DMBDGE. A second group shows slightly inferior phase behaviour but better coupling power than either HGE or BDGE: iBDGE, n-PDGE and 3-MBDGE. A third group shows good phase behaviour, like HGE but unlike BDGE, and better coupling power than HGE: CHMDGE, n-HDGE, 4-MPDGE and MIBCDGE.

Further evidence of the coupling power of some of the solvents or blends thereof when used with commercially available resins is shown in Tables 2–5 below. Coupling solvents of the present invention containing the claimed ethers and the methods of synthesis, where relevant, are further illustrated with reference to the following Examples:

EXAMPLES

1. Synthesis of 2-MBDGE

To a 5-liter three-necked round-bottomed flask equipped with a mechanical stirrer, thermometer, condenser and addition funnel was added diethylene glycol (3040 g, 28.6 moles). This was heated with stirring under nitrogen to 60° C. and a 50% aqueous solution of sodium hydroxide (225 g, 5.6 moles) added. The mixture was then heated to 93° C. and 1-chloro-2-methylbutane (594 g, 5.6 moles, containing 3–4% 1-chloro-3-methylbutane) was added dropwise over 3 hrs and heating and stirring continued for a further 60 hrs. The mixture was then allowed to cool. From this mixture, a liquid layer was collected. The solid salts remaining as residue in the mixture after removal of the liquid layer were extracted with dichloromethane (2500 ml) and removed by filtration. The liquid layer and the dichloromethane extract were combined and distilled water (3000 ml) added thereto and then vigorously mixed. The resultant mixture was allowed to separate into two layers, namely an organic layer and an aqueous layer. The organic layer was collected and again washed twice more with water until no diethylene glycol could be detected in the organic layer by GLC. The washed organic layer was then dried by passage through a compacted pad of anhydrous sodium sulphate. Dichloromethane was removed from the dried organic layer by flash distillation followed by distillation through a 2.54 cm, 5-plate Oldershaw column under high vacuum. 2-MBDGE (378 g, 38% yield) was collected as a colourless mobile liquid boiling at 82° C./1 mm Hg. The structure of this product was confirmed by $^{13}$C NMR spectroscopy recorded at ambient temperature which also showed the presence of 3–4% of the corresponding 3-methyl isomer. The following shows the detailed $^{13}$C NMR spectral assignments referenced to CDCl$_3$ at 77.1 ppm:

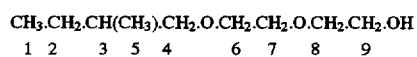

C1(10.7); C2(25.6); C3(34.2); C4(76.1); C5(15.9); C6(69.8); C7(69.8); C8(72.1); and C9(60.9) ppm.

The glycol ether had a boiling point of about 240° C. at ambient temperature and pressure.

2. Synthesis of 3,3-DMBGDE

To a 1-liter three-necked round-bottomed flask equipped with a mechanical stirrer, thermometer, condenser and addition funnel was added diethylene glycol (440 g, 4.1 moles).

A 50% aqueous solution of sodium hydroxide (32 g, 0.8 moles) was added to the glycol and the mixture heated with stirring under nitrogen to 100° C. for 1 hr. 1-Chloro-3,3-dimethylbutane (100 g, 0.8 moles) was then added dropwise over 1 hr and heating and stirring continued for a further 18 hrs. The mixture which was yellow was then allowed to cool. To the cold reaction mixture was added water (1080 ml) and dichloromethane (410 ml) and then vigorously mixed. The resultant mixture was allowed to separate into two layers, namely an organic layer and an aqueous layer. The organic layer was collected and again washed with water (100 ml). At this stage no diethylene glycol could be detected in the organic layer by GLC. The washed organic layer was then dried by passage through a compacted pad of anhydrous sodium sulphate. Dichloromethane was removed from the dried organic layer by flash distillation to give a yellow oil. This was then purified by fractional distillation through a 5-plate, 2.54 cm Oldershaw column under high vacuum. 3,3-DMBDGE (33 g, 21% yield) was collected as a colourless mobile liquid boiling at 118° C./9 mm Hg. This product had a purity of >99% as determined by gas-liquid chromatography (corresponding to the area % by integration of peaks). The structure of this product was confirmed by $^1$H and $^{13}$C NMR spectroscopy recorded at ambient temperature. The following shows the detailed $^{13}$C NMR spectral assignments referenced to $CDCl_3$ at 77.1 ppm and the $^1$H NMR spectral assignments are reference to residual $CHCl_3$ in $CDCl_3$ at 7.24 ppm:

$$H_3(CH_3)C(CH_3).CH_2.CH_2.O.CH_2.CH_2.O.CH_2.CH_2.OH$$
$$1\ \ 2\ \ 4\ 3\ \ \ \ 5\ \ \ \ 6\ \ \ \ \ 7\ \ \ 8\ \ \ \ \ 9\ \ \ 10$$

C1(29.7); C2(29.7); C3(29.7); C4(29.2); C5(42.4); C6(68.5); C7(69.9); C8(70.2); C9(72.4); and C10(61.2) ppm.

The $^1$H NMR spectrum showed the hydrogens on the following carbons: C1,C2 and C3 (0.75, singlet 9H); C5 (1.36 triplet 2H); C6 (3.31, triplet 2H); and C7, C8, C9 and C10, and OH (3.35–3.6 multiplets 9H).

3. Synthesis of CHMDGE

To a 2-liter three-necked round-bottomed flask equipped with a mechanical stirrer, thermometer, condenser and addition funnel was added diethylene glycol (596 g, 5.6 moles). A 50% aqueous solution of sodium hydroxide (45 g, 1.1 moles) was added to the glycol and the mixture heated with stirring under nitrogen to 100° C. for 1 hr. Cyclohexylmethyl bromide (200 g, 1.1 moles) was then added dropwise over 1 hr and heating and stirring continued for a further 18 hrs. The mixture was then allowed to cool. To the cold reaction mixture was added water (1800 ml) and dichloromethane (680 ml) and then vigorously mixed. The resultant mixture was allowed to separate into two layers, namely an organic layer and an aqueous layer. The organic layer was collected and again washed with water (200 ml). The washed organic layer was then dried by passage through a compacted pad of anhydrous sodium sulphate. Dichloromethane was removed from the dried organic layer by flash distillation to give an oil. This was then purified by fractional distillation through a 5-plate, 2.54 cm Oldershaw column under high vacuum. CHMDGE (69 g, 30% yield) was collected as a colourless mobile liquid boiling at 144° C./8 mm Hg. This product had a purity of >99% as determined by gas-liquid chromatography (corresponding to the area % by integration of peaks). The structure of this product was confirmed by $^1$H and $^{13}$C NMR spectroscopy recorded at ambient. The following shows the detailed $^{13}$C NMR spectral assignments referenced to $CDCl_3$ at 77.1 ppm and the $^1$H NMR spectral assignments are reference to residual $CHCl_3$ in $CDCl_3$ at 7.24 ppm:

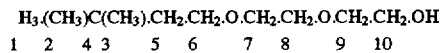

$$C_6H_{11}.CH_2.O.CH_2.CH_2.O.CH_2.CH_2.OH$$
$$1\text{--}6\ \ \ 7\ \ \ \ \ 8\ \ \ \ 9\ \ \ \ \ 10\ \ \ 11\ \ \ 12$$

C1(37.3); C2(29.5); C3(25.3); C4(26.1); C5(25.3); C6(29.5); C7(76.7); C8(69.9); C9(69.9); C10(72.2); and C11(61.0) ppm.

The tentative assignments of $^1$H NMR spectrum are as follows:

| | |
|---|---|
| hydrogens on C3, C5 axial | 0.66 ppm (multiplet, 2H) |
| hydrogens on C2, C4, C6 axial | 0.90 ppm (multiplet, 3H) |
| hydrogens on C1 axial, C2–C6) equatorial | 1.2–1.7 ppm (multiplet, 6H) |
| hydrogens on C7 | 3.0 ppm (doublet, 2H) |
| hydrogens on C8–C11 and on C12 | 3.2–3.7 ppm (multiplet, 9H) |

4. Synthesis of MIBCDGE

To a 5-liter three-necked round-bottomed flask equipped with a mechanical stirrer, thermometer, condenser and addition funnel was added dry 1,4-dioxan (1000 ml), 1,2-dimethoxyethane (1000 ml) and, with stirring under nitrogen, sodium hydride powder (86.6 g, 3.6 moles). The mixture was heated to 80° C. and dry 4-methyl-2-pentanol (369 g, 3.6 moles) added dropwise over 4 hrs. Hydrogen gas was evolved steadily and when the pentanol addition was complete the reaction mixture was heated to 97° C. After 3 hrs hydrogen gas evolution ceased and a dark mixture was formed. To this dark, homogeneous reaction mixture was added dropwise over 2.5 hrs tetrahydro-2-[2-(2-chloroethoxy)-ethoxy]-2H-pyran (753 g, 3.6 moles). The resultant mixture was then heated to 104° C. for a further 1.5 hrs. Thereafter, the reaction mixture was cooled and filtered through a compacted pad of Celite®.

Methanol (6000 ml) and Amberlyst®15 ion-exchange resin (110 g dry weight, pre-washed with methanol) were added to the crude filtered reaction product. The mixture so formed was heated to 45° C. with stirring for 1 hr to effect a transacetalisation reaction. The mixture was then cooled and filtered to recover the Ameberlyst® resin and a filtrate. To the filtrate was added potassium carbonate (4 g) and the resultant mixture subjected to flash distillation to remove methanol and other low boiling impurities therein so as to leave behind an oily product. To this oily product was added a further aliquot of methanol (1000 ml), stirred and then filtered through the recovered Amberlyst® resin. This transacetalisation procedure was repeated twice more using fresh Amberlyst® resin each time. When the low boiling components had been removed for the final time, the oil remaining was distilled under high vacuum in the presence of solid potassium carbonate (1 g) through a 5-plate, 2.54 cm Oldershaw column. MIBCDGE (50 g, 7% yield) was collected as a colourless mobile liquid boiling at 80° C./0.4 mm Hg. This product had a purity of >99% as determined by gas-liquid chromatography (corresponding to the area % by integration of peaks). The structure of this product was confirmed by $^1$H and $^{13}$C NMR spectroscopy recorded at ambient temperature. The following shows the detailed $^{13}$C NMR spectral assignments referenced to $CDCl_3$ at 77.1 ppm and the $^1$H NMR spectral assignments are reference to residual $CHCl_3$ in $CDCl_3$ at 7.24 ppm:

CH₃.CH(CH₃).CH₂.CH(CH₃).O.CH₂.CH₂.O.CH₂.CH₂.OH

| a | b | a' | c | d | e | f | g | h | i | j |
|---|---|----|---|---|---|---|---|---|---|---|
| 5 | 4 | 6  | 3 | 2 | 1 |   | 7 | 8 | 9 | 10 |

¹H NMR:

| | |
|---|---|
| a,a' | 0.57 (two doublets very close in shift) intesity 6H |
| b | 1.41 (multiplet) intensity 1H |
| c | 1.17, 0.85 (two multiplets, as 2Hs on C are not equivalent) total intensity 2H |
| d,f,g,h,i,j | 3.05–3.7 (multplets, intensity 10H |
| e | 0.80 doublet, intensity 3H |

¹³C NMR:

| | |
|---|---|
| C1 | 19.1 |
| C2 | 73.6 |
| C3 | 45.4 |
| C4 | 24.0 |
| C5 | 22.0) may be |
| C6 | 22.5) reversed |
| C7 | 67.0 |
| C8 | 70.0 |
| C9 | 72.0 |
| C10 | 60.8 |

5. Use of Ethers of the Present Invention as Cosolvents

The performance of the ethers of the present invention as a cosolvent in aqueous heptane systems and their comparison with the performance of HGE is tabulated in Table 1 below. In the table, the binary mixture is that of the glycol ether (30% by weight) and n-heptane (70% by weight) and the ternary mixture is derived by gradually adding water (% by weight) to a homogeneous solution of the ether (30% by weight) and heptane (70% by weight):

TABLE 1

| | TERNARY MIXTURE Amount of water added (% by wt) | |
|---|---|---|
| SOLVENT USED | Homogeneous | 2-Phases |
| HGE* | 1 | 1.5 (d) |
| BDGE* | 2 | 2.5 (nd) |
| iso-BDGE | 3 | 4 (nd) |
| n-PDGE | 5 | 5.5 (nd) |
| BGE* | 3 | 3.5 (d) |
| 3,3-DMBDGE | 4.5 | 5 (d) |
| CHMDGE | 2 | 2.5 (d) |
| 3-MBDGE | 6 | 7 (nd) |
| 2-MBDGE | 5 | 6 (d) |
| n-HDGE | 1.5 | 2 (d) |
| 4-MPDGE | 1.5 | 2 (d) |
| MIBCDGE | 1.5 | 2 (d) |

\* - comparative test not according to the invention
(nd) - substantial second phase having <50% wt/wt of water
(d) - droplets of second phase having >50% wt/wt of water The performance of some of the glycol ethers of the present invention, or mixtures of these glycol ethers, as cosolvents or blends of cosolvents for aqueous resin systems and their comparison with some commercially available coupling solvents is shown in Tables 2–5 below. In the Tables, the binary mixture is that of the glycol ether (or mixed glycol ethers as appropriate) and resin, either 30:70% w/w or 40:60% w/w, and the ternary mixture is derived by gradually adding water (% w/w) to the homogeneous mixture of glycol ether and resin.

TABLE 2

Alkyd Resin Synagua 3566 (70% w/w, ex Cray Valley Paints) and Cosolvent (30% w/w)

| | TERNARY MIXTURE Amount of water added (% by wt) | |
|---|---|---|
| COSOLVENT USED | Homogeneous | 2-Phases |
| 2-MBDGE | 7.0 | 7.2 |
| 3-MBDGE | 8.2 | 8.8 |
| n-PDGE | 8.2 | 8.5 |
| 2-MBDGE (30%)/ 3-MBDGE (5%)/ n-PDGE (65%) | 7.8 | 8.1 |
| BGE* | 6.5 | 7.2 |

\* - Comparative Test not according to the invention

TABLE 3

Alkyd Resin Synagua 359 (70% w/w, ex Cray Valley Paints) and Cosolvent (30% w/w)

| | TERNARY MIXTURE Amount of water added (% by wt) | |
|---|---|---|
| COSOLVENT USED | Homogeneous | 2-Phases |
| n-PDGE | 6.1 | 6.5 |
| BDGE* | 5.4 | 6.0 |

\* - Comparative Test not according to the invention

TABLE 4

Alkyd Resin Joncryl 586 (60% w/w, ex S C Johnson Polymer, The Netherlands) and Cosolvent (40% w/w)#

| | TERNARY MIXTURE Amount of water added (% by wt) | |
|---|---|---|
| COSOLVENT USED | Homogeneous | 2-Phases |
| 3-MBDGE | 7.1 | 7.7 |
| n-PDGE | 6.9 | 7.5 |
| 2-MBDGE (30%)/ 3-MBDGE (5%)/ n-PDGE (65%) | 7.05 | 7.6 |
| BDGE* | 6.5 | 7.0 |
| HGE* | 0 | 2.6 |

\* - Comparative Test not according to the invention
- Average figure from two sets of experiments

TABLE 5

Alkyd Resin Croda N2/634 (60% w/w) and Cosolvent (40% w/w)

| | TERNARY MIXTURE Amount of water added (% by wt) | |
|---|---|---|
| COSOLVENT USED | Homogeneous | 2-Phases |
| 2-MBDGE | 4.9 | 5.6 |
| HGE* | 3.7 | 4.2 |

\* - Comparative Test not according to the invention

We claim:

1. An aqueous resin formulation comprising as a coupling solvent a branched alkoxy ethoxyethanol characterized in that, the alkoxy ethoxyethanol:

i. has 4–8 carbon atoms in the alkoxy group, ii. has a boiling point at atmospheric pressure within the range from 200° to 350° C. and iii. in mixtures with n-heptane in the ratio of 30:70 by weight respectively, either a. does not cause phase separation, whereby the mixture remains homogenous until more than 2.5% w/w of water is added, and/or, b. phase separation occurs in the form of droplets upon addition of at least 1.5% w/w of water, said droplets having >50% w/w of water.

2. The aqueous resin formulation of claim 1 wherein said alkoxy ethoxyethanol is 3,3-Dimethylbutoxy ethoxyethanol.

3. The aqueous resin formulation of claim 1 wherein said alkoxy ethoxyethanol is Cyclohexylmethyleneoxy ethoxyethanol.

* * * * *